(12) United States Patent
Brenner (10) Patent No.: US 11,798,262 B2
(45) Date of Patent: *Oct. 24, 2023

(54) METHODS AND SYSTEMS FOR IDENTIFYING INTERNAL CONDITIONS IN JUVENILE FISH THROUGH NON-INVASIVE MEANS

(71) Applicant: Aquaticode Ltd., Birkirkara (MT)

(72) Inventor: Ayal Brenner, Birkirkara (MT)

(73) Assignee: AQUATICODE LTD, Birkirkara (MT)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,587

(22) Filed: Feb. 11, 2022

(65) Prior Publication Data

US 2022/0172363 A1 Jun. 2, 2022

Related U.S. Application Data

(63) Continuation of application No. 16/984,496, filed on Aug. 4, 2020, now Pat. No. 11,282,199.

(Continued)

(51) Int. Cl.
*G06V 10/764* (2022.01)
*G06T 7/90* (2017.01)
(Continued)

(52) U.S. Cl.
CPC ......... *G06V 10/764* (2022.01); *C12Q 1/6809* (2013.01); *G06F 18/214* (2023.01); *G06N 3/02* (2013.01); *G06T 7/0012* (2013.01); *G06T 7/90* (2017.01); *G06V 10/7753* (2022.01); *G06V 10/82* (2022.01); *G06V 20/50* (2022.01); *G06V 20/60* (2022.01); *G06V 20/70* (2022.01); *G06T 2207/10016* (2013.01); (Continued)

(58) Field of Classification Search
None
See application file for complete search history.

(56) References Cited

U.S. PATENT DOCUMENTS

| 9,104,906 B2 | 8/2015 | McVey |
| 11,282,199 B2 * | 3/2022 | Brenner ............... G06T 7/0012 |

(Continued)

FOREIGN PATENT DOCUMENTS

| GB | 2201772 A | 9/1988 |
| JP | 6826356 B1 | 2/2021 |

(Continued)

OTHER PUBLICATIONS

Munhofen, Jennifer L., et al. "Comparing ultrasonography and endoscopy for early gender identification of juvenile Siberian sturgeon." North American Journal of Aquaculture 76.1 (2014): 14-23. (Year: 2014).*

(Continued)

*Primary Examiner* — Sean M Conner
(74) *Attorney, Agent, or Firm* — Pillsbury Winthrop Shaw Pittman LLP (57) ABSTRACT

Methods and systems are disclosed for improvements in aquaculture that allow for increasing the number and harvesting efficiency of fish in an aquaculture setting by identifying and predicting internal conditions of the juvenile fish based on external characteristics that are imaged through non-invasive means.

28 Claims, 6 Drawing Sheets

Related U.S. Application Data (60) Provisional application No. 62/956,759, filed on Jan. 3, 2020, provisional application No. 62/956,764, filed on Jan. 3, 2020, provisional application No. 62/956,751, filed on Jan. 3, 2020, provisional application No. 62/889,313, filed on Aug. 20, 2019.

(51) Int. Cl.

| | |
|---|---|
| *C12Q 1/6809* | (2018.01) |
| *G06T 7/00* | (2017.01) |
| *G06V 20/70* | (2022.01) |
| *G06V 10/82* | (2022.01) |
| *G06V 20/60* | (2022.01) |
| *G06V 20/50* | (2022.01) |
| *G06V 10/774* | (2022.01) |
| *G06F 18/214* | (2023.01) |
| *G06N 3/02* | (2006.01) |
| *G06V 20/68* | (2022.01) |

(52) U.S. Cl.
CPC ............... *G06T 2207/10024* (2013.01); *G06T 2207/10048* (2013.01); *G06T 2207/20081* (2013.01); *G06T 2207/20084* (2013.01); *G06V 20/68* (2022.01)

(56) References Cited

U.S. PATENT DOCUMENTS

| | | |
|---|---|---|
| 2020/0170226 A1 | 6/2020 | Aas |
| 2021/0142052 A1 | 5/2021 | James et al. |

FOREIGN PATENT DOCUMENTS

| | | |
|---|---|---|
| NO | 20170365 A1 | 9/2018 |
| WO | 2012/154841 A2 | 11/2012 |
| WO | 2018/011744 A1 | 1/2018 |
| WO | 2022/131929 A1 | 6/2022 |
| WO | 2022131929 A1 | 6/2022 |

OTHER PUBLICATIONS

Abe, Shuji, and Hiroaki Ishihata. "Trial to determine the sex of salmon using CNN." Annual Conference of the Japanese Society for Artificial Intelligence, JSAI2019 (4H3J1303). 2019. (Year: 2019).*
Dongyoon Han et al., "Deep Pyramidal Residual Networks", https://arxiv.org/abs/1610.02915 Cornell University, submitted Oct. 10, 2016, 8 pgs.
Ningning Ma et al., "SHUFFLENET V2: Practical Guidelines for Efficient CNN Architecture Design", https://arxiv.org/abs/1807.11164 Cornell University, submitted Jul. 30, 2018, 19, pgs.
Proteek Chandan Roy et al., "Mitigating Information Leakage in Image Representations: A Maximum Entropy Approach", https://arxiv.org/abs/1904.05514 Cornell University, submitted on Apr. 11, 2019, 11 pgs.
Mark Sandler et al., "MobileNetV2: Inverted Residuals and Linear Bottlenecks", https://arxiv.org/abs/1801.04381 The IEEE Conference on Computer Vision and Pattern Recognition (CVPR), 2018, pp. 4510-4520.
Yoshihiro Yamada et al., "ShakeDrop Regularization for Deep Residual Learning", https://arxiv.org/abs/1802.02375 IEEE Access, 7, 1, pp. 186126-186136, 2019.
Sergey Zagorukyo et al., "Wide Residual Networks", https://arxiv.org/abs/1605.07146 Cornell University, submitted on May 23, 2016, 15 pgs.
International Search Report and Written Opinion issued in corresponding PCT Patent Application No. PCT/EP2020/071937, dated Jan. 13, 2021.
International Search Report and Written Opinion issued in corresponding PCT Patent Application No. PCT/EP2020/071939, dated Jan. 13, 2021.
Dowlati, Majid et al.: "Freshness assessment of gilthead sea bream (Sparus Aurata) by machine vision based on gill and eye color changes", Journal of Food Engineering, vol. 119, No. 2, Nov. 1, 2013.
Hassoun, Abdo et al.: "Quality Evaluation of Fish and Other Seafood by Traditional and Nondestructive Instrumental Methods: Advantages and Limitations", Critical Reviews in Food Science and Nutrition, vol. 57, No. 9, Mar. 10, 2017.
Fabregas, Aleta C. et al.: "SUGPO: A White Spot Disease Detection in shrimps Using Hybrid Neural Networks with Fuzzy Logic Algorithm" Information Technology: IOT and Smart City, Dec. 29, 2018.
Navotas, Ian C. et al.: "Fish identification and freshness classification through image processing using artificial neutral network", ARPN Journal of engineering and Applied Sciences, vol. 13, No. 18, Sep. 1, 2018.
Sengar, Namita et al.: "Computer vision based technique for identification of fish quality after pesticide exposure", International Journal of Food Properties, Dec. 28, 2017.
International Search Report and Written Opinion issued in corresponding PCT Patent Application No. PCT/EP2020/071938, dated Mar. 9, 2021.
Meidell, Espen et al.: "FishNet: A Unified Embedding for Salmon Recognition (Master's thesis)", Retrieved from the Internet: URL:https://ntnuopen.ntnu.no/ntnu-xmlui/bitstream/handle/11250/2628799/no.ntnu%3ainspera%3a2515311.pdf? sequence=I&isAnowed=y[retrieved on Dec. 17, 2020], XPO55761171, Jun. 7, 2019.
Xu, Zhiping et al.: "Zebrafish tracking using convolutional neural networks", Scientific Reports, vol. 7, Feb. 17, 2017, XP055761425.
Delcourt, Johann et al.: Individual identification and marking techniques for zebrafish, Reviews Impish Biology and Fisheries, vol. 28, No. 4, Sep. 6, 2018, (Sep. 6, 2018), pp. 839-864, XP036635195.
De Almeida, Diana Bastos Serrano. "Gonad Differentiation in Guppy Fish and Testing Strategies for the Production of Sterile and All-Female Offspring." (2016). (Year: 2016).
Zion, B., et al. "Classification of guppies'(Poecilia reticulata) gender by computer vision." Aquacultural Engineering 38.2 (2008): 97-104. (Year: 2008).
Zion, Boaz. "The use of computer vision technologies in aquaculture—a review." Computers and electronics in agriculture 88 (2012): 125-132. (Year: 2012).
Nilsen, H., et al. "Visible/near-infrared spectroscopy: a new tool for the evaluation of fish freshness?." Journal of Food Science 67.5 (2002): 1821-1826. (Year: 2002).
Maitre, Diane, et al. "Sex differentiation in grayling (Salmonidae) goes through an all-male stage and is delayed in genetic males who instead grow faster." Scientific reports 7.1 (2017): 1-11. (Year: 2017).
Abe, Shuji et al. "Trial to Determine the Sex of Salmon Using CNN" 33rd Annual Conference of the Japanese Society for Artificial Intelligence. (2019). 1-4. (Year: 2019).
Fablet, Ronan, and Nicolas Le Josse. "Automated fish age estimation from otolith images using statistical learning." Fisheries Research 72.2-3 (2005): 279-290. (Year: 2005).
Lee, Hansang, Minseok Park, and Junmo Kim. "Plankton classification on imbalanced large scale database via convolutional neural networks with transfer learning." 2016 IEEE international conference on image processing (ICIP). IEEE, 2016. (Year: 2016).
Merz, Joseph E., and William R. Merz. "Morphological features used to identify Chinook salmon sex during fish passage." The Southwestern Naturalist 49.2 (2004): 197-202. (Year: 2004).
Collhueque, Nelson. "Genetics of salmonid skin pigmentation: clues and prospects for improving the external appearance of farmed salmonids." Reviews in Fish Biology and Fisheries 20.1 (2010): 71-86. (Year: 2010).
International Preliminary Report on Patentability and Written Opinion issued in PCT Patent Application No. PCT/EP/2020/071937, dated Mar. 3, 2022, 10 pages.
International Preliminary Report on Patentability and Written Opinion issued in PCT Patent Application No. PCT/EP/2020/071938, dated Mar. 3, 2022, 14 pages.

(56) References Cited

OTHER PUBLICATIONS

International Preliminary Report on Patentability and Written Opinion issued in PCT Patent Application No. PCT/EP/2020/071939, dated Mar. 3, 2022, 11 pages.

Dowlati, M. et al.: "Freshness assessment of gilthead sea bream (Sparus aurata) by machine vision based on gill and eye color changes", Journal of Food Engineering, vol. 119, No. 2, Nov. 1, 2013, pp. 277-287.

Navotas, I.C. et al.: "Fish Identification and Freshness Classification Through Image Processing Using Artificial Neural Network", ARPN Journal of Engineering and Applied Sciences, vol. 13, No. 18, Sep. 1, 2018.

Sengar, N. et al.: "Computer vision based technique for identification of fish quality after pesticide exposure", International Journal of Food Properties, Dec. 28, 2017, vol. 20, No. S2, pp. 1-15.

Meidell, E. et al.: "FishNet: A Unified Embedding for Salmon Recognition", Trondheim, Jun. 7, 2019, 8 pages.

Xu, Z. et al.: "Zebrafish tracking using convolutional neural networks", Scientific Reports, vol. 7, Feb. 11, 2017, 11 pages.

Delcourt, J. et al.: "Individual identification and marking techniques for zebrafish", Rev. Fish Biol. Fisheries, vol. 28, No. 4, Sep. 6, 2018, pp. 839-864.

Hassoun, A. et al.: "Quality evaluation of fish and other seafood by traditional and nondestructive instrumental methods: Advantages and limitations", Critical Reviews in Food Science and Nutrition, vol. 57, No. 9, Mar. 10, 2017, pp. 1976-1998.

Fabregas, A. C. et al.: "SUGPO: A White Spot Disease Detection in Shrimps Using Hybrid Neural Networks with Fuzzy Logic Algorithm", Association for Computing Machinery, Dec. 29, 2018, pp. 199-203.

Communication pursuant to Rule 114(2) EPC dated Jul. 26, 2023, which issued in EP Application No. 22209058.1.

\* cited by examiner

100

| Biomarker | Eggs | | Fries | |
|---|---|---|---|---|
| | p-value | Accuracy | p-value | Accuracy |
| SSA0139ECIG (T:T vs T:G and G:G) | 0.002 | 77% | <0.00001 | 72% |
| RAD_HT16 (A:A vs A:G and G:G) | <0.00001 | 88% | <0.00001 | 71% |
| rs863507253_ht01 (A:A vs T:A) | 0.001 | 93% | <0.00001 | 85% |
| rs863338084 (T:T vs C:T and C:C) | 0.005 | 73% | <0.00001 | 56% |

METHODS AND SYSTEMS FOR IDENTIFYING INTERNAL CONDITIONS IN JUVENILE FISH THROUGH NON-INVASIVE MEANS

CROSS-REFERENCE TO RELATED APPLICATIONS

The subject application is a continuation of U.S. patent application Ser. No. 16/984,496, filed Aug. 4, 2020, which claims priority to U.S. Provisional Patent Application No. 62/889,313, filed Aug. 20, 2019; U.S. Provisional Application No. 62/956,751, filed Jan. 3, 2020; U.S. Provisional Application No. 62/956,759, filed Jan. 3, 2020; and U.S. Provisional Patent Application No. 62/956,764, filed Jan. 3, 2020. The subject matter of each of which is incorporated herein by reference in entirety.

FIELD OF THE INVENTION

The invention relates to identifying internal conditions in juvenile fish.

BACKGROUND

Aquaculture, the farming of fish, crustaceans, mollusks, aquatic plants, algae, and other organisms, is the fastest growing food sector, and it provides most fish for human consumption. However, there is a rising demand for seafood due to human population growth, increasing disposable income in the developing world (which coincides with an increase of a meat-based diet), increasing coastal populations, and general health awareness (which tends to motivate consumers to fish-based protein). Wild fish resources are already at their limits, and the world market is increasingly focusing on being more sustainable and environmentally responsible, meaning increased harvesting of wild fish is not feasible.

SUMMARY

Given the infeasibility of meeting the world demand through harvesting wild fish, aquaculture represents a natural solution. However, increasing the use of aquaculture raises additional concerns such as increased disease, growth and feeding inefficiencies, and waste management. For example, increasing the number of fish in a fish farm, without mitigating measures, increases the prevalence of diseases as the proximity of fish to each other increases. The growth and feed inefficiencies are increased as more fish in proximity to each other make tracking fish size and effectively distributing feed more difficult, and more fish lead to more fish waste which increases the environmental impact of a fish farm on its immediate area.

Methods and systems are disclosed herein for improvements in aquaculture that allow for increasing the number and harvesting efficiency of fish in an aquaculture setting while still mitigating the problems above. Specifically, through a selective breeding and monitoring program of juvenile fish, juvenile fish with superior traits are identified and sorted. In conventional systems, fish sorting is not possible until fish mature to over 50 grams. At this time, ultrasound technology can be used to determine traits such as gender. Prior to 50 grams, invasive genetic tests can be done to determine gender and identify biomarkers related to certain diseases, but these genetic tests may result in the death of the specimen (e.g., crushing of the fertilized egg).

In contrast to the conventional approaches, methods and systems are described herein for non-invasive procedures for identifying traits in juvenile fish. Moreover, based on the methods and systems described herein, certain traits can be determined when the juvenile fish is only 2-4 grams, and/or still in the egg, and with over 90% accuracy for certain genetic biomarkers. As this procedure is non-invasive and relies of the detection of phenotype characteristics based on external images of fish eggs and/or fish fries, the viability of the specimen is not threatened. Because the viability of the specimen is not threatened and the genetic traits are identified, the juvenile fish may be sorted for a given gender or disease resistance at a size and/or level of maturity unseen by conventional approaches. The efficiencies and number of fish available for farming are thus increased without the drawbacks discussed above.

Key to the advancements discussed above is the detection of certain phenotype characteristics, as discussed below, of the juvenile fish based on external images. As the number of specimens (e.g., eggs and/or fries) in a single batch may number in the tens of thousands, also important to these advancements is to efficiently detect the phenotype characteristics quickly and efficiently. To do this, the methods and systems discussed below described the use of trained artificial neural networks. These artificial neural networks are trained on data sets of juvenile fish in a particular life stage (e.g., fertilized egg, alevin, and/or young fry), at a particular age (e.g., under 1 year), and/or a particular size (e.g., 2-4 grams), and are based on image sets that include the phenotype characteristics.

In one aspect, methods and systems for identifying internal conditions in juvenile fish based on external characteristics are described. For example, the system may include receiving an image set of a first juvenile fish, wherein the image set of the first juvenile fish includes a phenotype characteristic of the first juvenile fish. In some embodiments, the juvenile fish may be a fry, and the image set of the juvenile fish may include an external first view image of the first fry and an external second view image of the first fry. Additionally or alternatively, the image set of the fry may be generated while the gills of the fry are hydrated or while the fry is sedated in order to reduce stress on the fry. In some embodiments, the juvenile fish may be a fertilized egg, and the image set of the juvenile fish may include a depth of field of about half of the fertilized egg. In some embodiments, the image set may be created using an imaging device that detects electromagnetic radiation with wavelengths between about 400 nanometers to about 1100 nanometers and/or different genders of juvenile fish may be imaged together. For example, by standardizing the collection and preparation of image sets of juvenile fish that contain the phenotype characteristics (e.g., by reducing stress, imaging genders together, normalizing specimen size, and/or using consistent image parameters), system bias can be eliminated.

The system may then generate a first pixel array based on the image set of the first juvenile fish and label the first pixel array with a genotype biomarker for the first juvenile fish. For example, the detected phenotype characteristics in the image set may be converted into a form that can be quickly and efficiently processed by an artificial neural network. In some embodiments, this may include one or more vectors, arrays, and/or matrices that represent either a Red, Green, Blue colored or grayscale images. Furthermore, in some embodiments, the system may additionally convert the image set from a set of one or more vectors, arrays, and/or matrices to another set of one or more vectors, arrays, and/or matrices. For example, the system may convert an image set having a red color array, a green color array, and a blue color to a grayscale color array.

The system may then train an artificial neural network to detect the genotype biomarker in juvenile fish based on the labeled first pixel array. For example, the system may generate the image set of the first juvenile fish, and genetically test the first juvenile fish to determine a genotype biomarker (e.g., SSA0139ECIG, RAD_HT16, rs863507253_ht01, rs863338084, and gender) in the first juvenile fish. The presence of a particular genotype biomarker is then correlated to one or more phenotype characteristics. For example, the artificial neural network may have classifications for the genotype biomarkers. The artificial neural network is then trained based on a first data set (e.g., including data of the first juvenile fish and others) to classify a specimen as having a given genotype biomarker when particular phenotype characteristics are present.

The system may then receive an image set of a second juvenile fish, wherein the image set of the second juvenile fish includes a phenotype characteristic of the second juvenile fish. The system may generate a second pixel array based on the image set of the second juvenile fish, and input the second pixel array into the trained neural network. The system may then receive an output from the trained neural network indicating that the second juvenile fish has the genotype biomarker. For example, the system may input a second data set (e.g., image sets of juvenile fish for which genotype biomarkers are not known) into the trained artificial neural network. The trained artificial neural network may then classify the image sets of juvenile fish into according to the genotype biomarkers. For example, the genotype biomarker for the first juvenile fish may be a first classification of the neural network, and the system may generate an output from the neural network indicating the second juvenile fish has the same genotype biomarker as the first juvenile fish based on matching the second pixel array to the first classification.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

Figure 1:
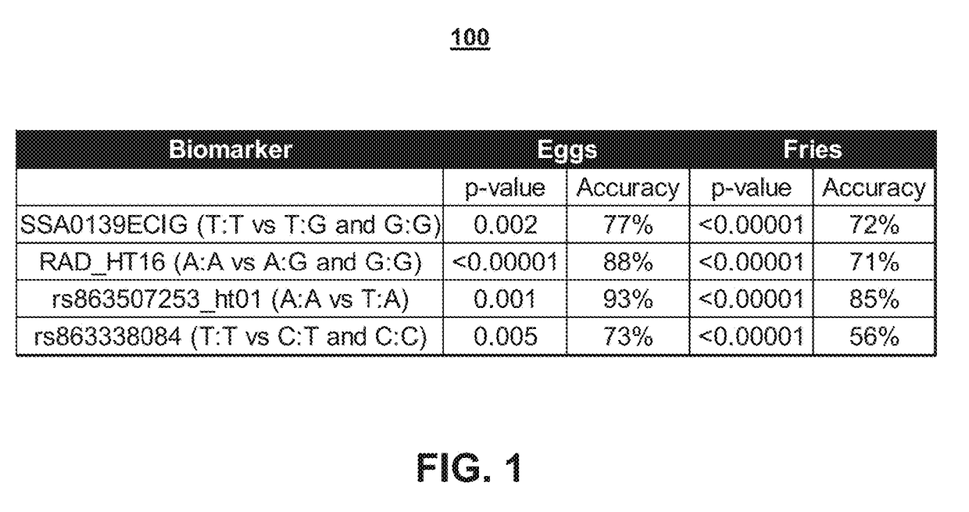
FIG. 1 shows a chart indicating the accuracy of external characteristics detection based on internal conditions, in accordance with one or more embodiments.

In contrast to conventional approaches to identifying internal conditions that use invasive approaches, methods and systems are described herein for non-invasive procedures that identifies genetic traits non-invasively and at an early stage in the life cycle of fish. FIG. 1 shows a chart indicating the accuracy of genotype biomarker detection based on phenotype characteristics, in accordance with one or more embodiments.

As shown in FIG. 1, four genotype biomarkers were used as classification for the artificial neural network. These genotype biomarkers included SSA0139ECIG, RAD_HT16, rs863507253_ht01, rs863338084, which are genotype biomarkers that indicate a resistance to the Infection Pancreatic Necrosis ("IPN") virus, a highly contagious virus that affects young fish, salmonids in particular. IPN is difficult to detect as the disease typically affects young fish (i.e., less than six months old), making testing for the disease difficult. FIG. 1 shows the results of the method and systems disclosed herein using either image sets based on fertilized eggs or fries. The accuracy for fertilized eggs ranged between 73 and 93%, while accuracy for the fries ranged between 56 and 85%.

As discussed in detail below, methods and systems for identifying and predicting internal conditions in juvenile fish based on external characteristics. The internal conditions may include a current physiological condition (e.g., a condition occurring normal in the body of the juvenile fish) such as a gender of the juvenile fish (e.g., as determined by the development of sex organs) and/or a stage of development in the juvenile fish (e.g., the state of smoltification). The internal conditions may include a predisposition to a future physiological condition such as a growth rate, maturity date, and/or behavioral traits. The internal condition may include a pathological condition (e.g., a condition centered on an abnormality in the body of the juvenile fish based in response to a disease) such as whether or not the juvenile fish is suffering from a given disease and/or is currently infected with a given disease. The internal condition may include a genetic condition (e.g., a condition based on the formation of the genome of the juvenile fish) such as whether or not the juvenile fish includes a given genotype. The internal condition may include a presence of a given biomarker (e.g., a measurable substance in an organism whose presence is indicative of a disease, infection, current internal condition, future internal condition, and/or environmental exposure).

As discussed below, these internal characteristics may be determined based on externally visible traits of the juvenile fish. These externally visible traits may include phenotype characteristics (e.g., one or more observable characteristics of the juvenile fish resulting from the interaction of its genotype with the environment). These externally visible traits may include traits corresponding to physiological changes in the juvenile fish. For example, during smoltification (i.e., the series of physiological changes where juvenile salmonid fish adapt from living in fresh water to living in seawater), externally visible traits related to this physiological change may include altered body shape, increased skin reflectance (silvery coloration), and increased enzyme production (e.g., sodium-potassium adenosine triphosphatase) in the gills.

In some embodiments, the system may include receiving an image set of a first juvenile fish. The image set may include one or more images of the juvenile fish. If the image set includes multiple images, the multiple images may be captured from different angles (e.g., a top view, side view, bottom view, etc.) and/or may be captured substantially simultaneously. The images in the image set may include separate images (e.g., images stored separately, but linked by a common identifier such as a serial number) or images stored together. An image in an image set may also be a composite image (e.g., an image created by cutting, cropping, rearranging, and/or overlapping two or more images. In some embodiments, the juvenile fish may be a fry, and the image set of the juvenile fish may include an external first view image of the first fry and an external second view image of the first fry. Additionally or alternatively, the image set of the fry may be generated while the gills of the fry are hydrated or while the fry is sedated in order to reduce stress on the fry. In some embodiments, the juvenile fish may be a fertilized egg, and the image set of the juvenile fish may include a depth of field of about half of the fertilized egg and/or a depth of field such that the image captures one or more of the vitelline membrane, chorion, yolk, oil globule, perivitelline space, or embryo.

In some embodiments, the image set may be created using an imaging device that detects electromagnetic radiation with wavelengths between about 400 nanometers to about 1100 nanometers. In some embodiments, the image set may be created using an imaging device that detects electromagnetic radiation with wavelengths between 400 to 500 nanometers, between 500 to 600 nanometers, between 700 to 900 nanometers, or between 700 to 1100 nanometers.

The image set may capture an image of a given specimen. The specimen may be a juvenile fish (e.g., a fish that has not reach sexual maturity). Juvenile fish may include fish eggs or larvae. Additionally, juvenile fish may refer to fish fry (e.g., a recently hatched fish that has reached the stage where its yolk-sac has almost disappeared and its swim bladder is operational to the point where the fish can actively feed for itself) or a fish fingerling (e.g., a fish that has reached the stage where the fins can be extended and where scales have started developing throughout the body). The juvenile fish may in some embodiments refer to salmon that have not yet completed the process of physiological changes that allows them to survive a shift from freshwater to saltwater (i.e., smoltification). It should be noted that while embodiments of this disclosure relate to juvenile fish, these embodiments are also applicable to other specimens. In particular, these specimens may include any type of aquatic life (e.g., organisms that live in aquatic ecosystems) and/or oviparous organisms.

In some embodiments, the system may then generate a pixel array based on the image set of the first juvenile fish. The pixel array may refer to computer data that describes the image (e.g., pixel by pixel). In some embodiments, this may include one or more vectors, arrays, and/or matrices that represent either a Red, Green, Blue or grayscale image. Furthermore, in some embodiments, the system may additionally convert the image set from a set of one or more vectors, arrays, and/or matrices to another set of one or more vectors, arrays, and/or matrices. For example, the system may convert an image set having a red color array, a green color array, and a blue color to a gray scale color array.

Figure 2:
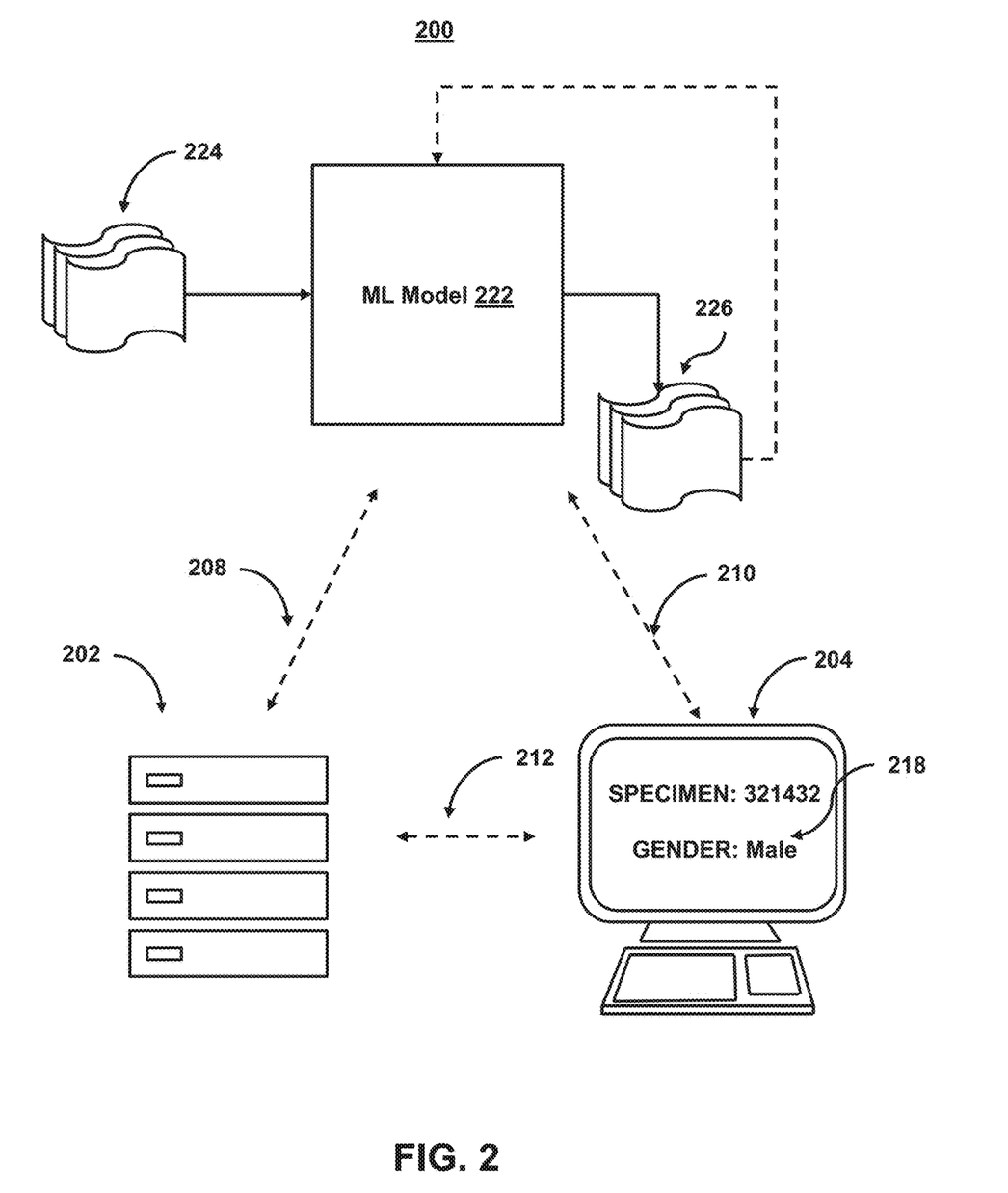
FIG. 2 shows a system featuring a machine learning model configured to detect internal conditions based on external characteristics, in accordance with one or more embodiments.

FIG. 2 shows a computer system featuring a machine learning model configured to detect internal conditions based on external characteristics, in accordance with one or more embodiments. As shown in FIG. 2, system 200 may include client device 202, client device 204 or other components. Each of client devices 202 and 204 may include any type of mobile terminal, fixed terminal, or other device. Each of these devices may receive content and data via input/output (hereinafter "I/O") paths and may also include processors and/or control circuitry to send and receive commands, requests, and other suitable data using the I/O paths. The control circuitry may comprise any suitable processing circuitry. Each of these devices may also include a user input interface and/or display for use in receiving and displaying data. By way of example, client devices 202 and 204 may include a desktop computer, a server, or other client device. Users may, for instance, utilize one or more client devices 202 and 204 to interact with one another, one or more servers, or other components of system 200. It should be noted that, while one or more operations are described herein as being performed by particular components of system 200, those operations may, in some embodiments, be performed by other components of system 200. As an example, while one or more operations are described herein as being performed by components of client device 202, those operations may, in some embodiments, be performed by components of client device 204. It should be noted that, although some embodiments are described herein with respect to machine learning models, other prediction models (e.g., statistical models or other analytics models) may be used in lieu of or in addition to machine learning models in other embodiments (e.g., a statistical model replacing a machine learning model and a non-statistical model replacing a non-machine-learning model in one or more embodiments).

Each of these devices may also include memory in the form of electronic storage. The electronic storage may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storage may store software algorithms, information determined by the processors, information obtained from servers, information obtained from client devices, or other information that enables the functionality as described herein.

FIG. 2 also includes communication paths 208, 210, and 212. Communication paths 208, 210, and 212 may include the Internet, a mobile phone network, a mobile voice or data network (e.g., a 4G or LTE network), a cable network, a public switched telephone network, or other types of communications network or combinations of communications networks. Communication paths 208, 210, and 212 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

In some embodiments, system 200 may use one or more prediction models to predict internal conditions based on external characteristics. For example, as shown in FIG. 2, system 200 may predict a genotype characteristic of a specimen (e.g., a juvenile fish identified by a specimen identification) using machine learning model 222. The determination may be output shown as output 218 on client device 204. The system may include one or more neural networks (e.g., as discussed in relation to FIG. 3) or other machine learning models.

As an example, with respect to FIG. 2, machine learning model 222 may take inputs 224 and provide outputs 226. The inputs may include multiple data sets such as a training data set and a test data set. The data sets may represent images (or image sets) of specimens such as juvenile fish. In one use case, outputs 226 may be fed back to machine learning model 222 as input to train machine learning model 222 (e.g., alone or in conjunction with user indications of the accuracy of outputs 226, labels associated with the inputs, or with other reference feedback information). In another use case, machine learning model 222 may update its configurations (e.g., weights, biases, or other parameters) based on its assessment of its prediction (e.g., outputs 226) and reference feedback information (e.g., user indication of accuracy, reference labels, or other information). In another use case, where machine learning model 222 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 222 may be trained to generate better predictions.

Machine learning model 222 may be trained to detect the internal conditions in juvenile fish based on a pixel array. For example, client device 202 or 204 may generate the image set of the first juvenile fish (e.g., via an image capture device), and genetically test the first juvenile fish to determine a genotype biomarker (e.g., SSA0139ECIG, RAD_HT16, rs863507253 ht01, rs863338084, and gender) in the first juvenile fish. The presence of a particular genotype biomarker is then correlated to one or more phenotype characteristics. For example, machine learning model 222 may have classifications for the internal conditions (e.g., genotype biomarkers). Machine learning model 222 is then trained based on a first data set (e.g., including data of the first juvenile fish and others) to classify a specimen as having a given genotype biomarker when particular phenotype characteristics are present.

The system may then receive an image set of a second juvenile fish, wherein the image set of the second juvenile fish includes an external characteristic of the second juvenile fish. Client device 202 or 204 may generate a second pixel array based on the image set of the second juvenile fish and input the second pixel array into machine learning model 222. The system may then receive an output from machine learning model 222 indicating that the second juvenile fish has the same internal condition (e.g., genotype biomarker) as the first. For example, the system may input a second data set (e.g., image sets of juvenile fish for which genotype biomarkers are not known) into machine learning model 222. Machine learning model 222 may then classify the image sets of juvenile fish into according to the genotype biomarkers. For example, the genotype biomarker for the first juvenile fish may be a first classification of machine learning model 222, and the system may generate an output from machine learning model 222 the second juvenile fish has the same genotype biomarker as the first juvenile fish based on matching the second pixel array to the first classification.

In some embodiments, system 200 is further configured to handle, sort, and/or transfer fish (e.g., for vaccination, gender segregation, transfer to sea or breeding area, etc.). In such embodiments, the internal condition may be detected based on external characteristics in real-time (e.g., as the juvenile fish are transported along a conveyor belt or otherwise transferred). That is, following the output of an internal condition (e.g., a genotype biomarker as described in FIG. 6 below), system 200 may sort the juvenile fish based on the determined internal condition.

Figure 3:
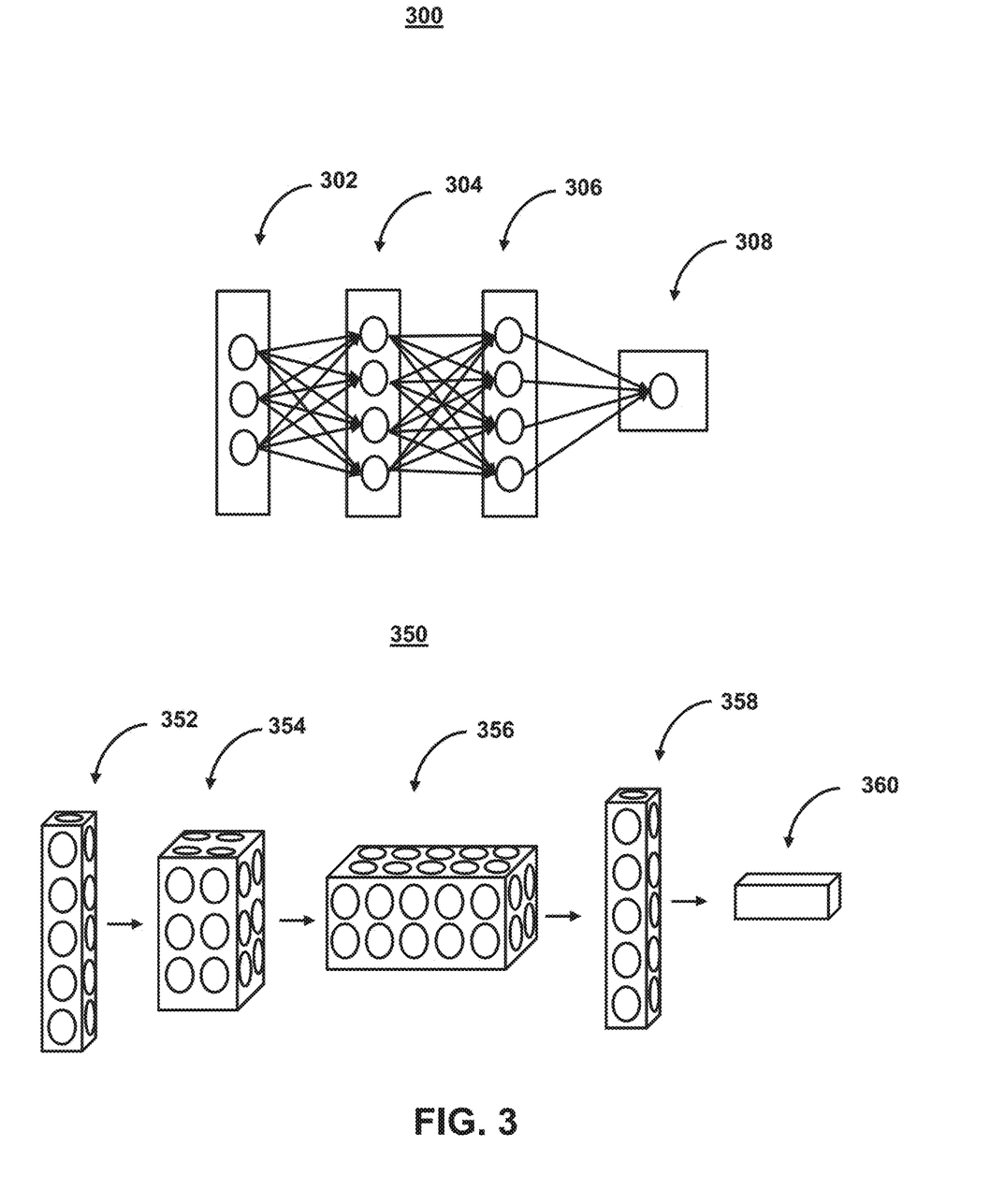
FIG. 3 shows graphical representations of artificial neural network models for detecting internal conditions based on external characteristics, in accordance with one or more embodiments.

FIG. 3 shows a graphical representations of artificial neural network models for internal condition (e.g., genotype biomarker) detection based on an external (e.g., phenotype) characteristics, in accordance with one or more embodiments. Model 300 illustrates an artificial neural network. Model 300 includes input level 302. Image sets of juvenile fish may be entered into model 300 at this level. Model 300 also includes one or more hidden layers (e.g., hidden layer 304 and hidden layer 306). Model 300 may be based on a large collection of neural units (or artificial neurons). Model 300 loosely mimics the manner in which a biological brain works (e.g., via large clusters of biological neurons connected by axons). Each neural unit of a model 300 may be connected with many other neural units of model 300. Such connections can be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Model 300 may be self-learning and trained, rather than explicitly programmed, and can perform significantly better in certain areas of problem solving, as compared to traditional computer programs. During training, output layer 308 may corresponds to a classification of model 300 (e.g., whether or not a given image set corresponds to a genotype biomarker) and an input known to correspond to that classification may be input into input layer 302. In some embodiments, model 300 may include multiple layers (e.g., where a signal path traverses from front layers to back layers). In some embodiments, back propagation techniques may be utilized by model 300 where forward stimulation is used to reset weights on the "front" neural units. In some embodiments, stimulation and inhibition for model 300 may be more free-flowing, with connections interacting in a more chaotic and complex fashion. Model 300 also includes output layer 308. During testing, output layer 308 may indicate whether or not a given input corresponds to a classification of model 300 (e.g., whether or not a given image set corresponds to a genotype biomarker).

FIG. 3 also includes model 350, which is a convolutional neural network. The convolutional neural network is an artificial neural network that features one or more convolutional layers. Convolution layers extract features from an input image. Convolution preserves the relationship between pixels by learning image features using small squares of input data. For example, the relationship between the individual parts of the fertilized egg (e.g., vitelline membrane, chorion, yolk, oil globule, perivitelline space, and/or embryo) may be preserved. In another example, the relationship between the individual parts of the fry (e.g., dorsal fin, caudal fin, operculum, pectoral fin, gills, and/or scale formation) may be preserved. As shown in model 350, input layer 352 may proceed to convolution blocks 354 and 356 before being output to convolutional output 358. In some embodiments, model 350 may itself serve as an input to model 300.

In some embodiments, model 350 may implement an inverted residual structure where the input and output of a residual block (e.g., block 354) are thin bottleneck layers. A residual layer may feed into the next layer and directly into layers that are one or more layers downstream. A bottleneck layer (e.g., block 358) is a layer that contains few neural units compared to the previous layers. Model 350 may use a bottleneck layer to obtain a representation of the input with reduced dimensionality. An example of this is the use of autoencoders with bottleneck layers for nonlinear dimensionality reduction. Additionally, model 350 may remove non-linearities in a narrow layer (e.g., block 358) in order to maintain representational power. In some embodiments, the design of model 350 may also be guided by the metric of computation complexity (e.g., the number of floating point operations). In some embodiments, model 350 may increase the feature map dimension at all units to involve as many locations as possible instead of sharply increasing the feature map dimensions at neural units that perform downsampling. In some embodiments, model 350 may decrease the depth and increase width of residual layers in the downstream direction.

Figure 4:
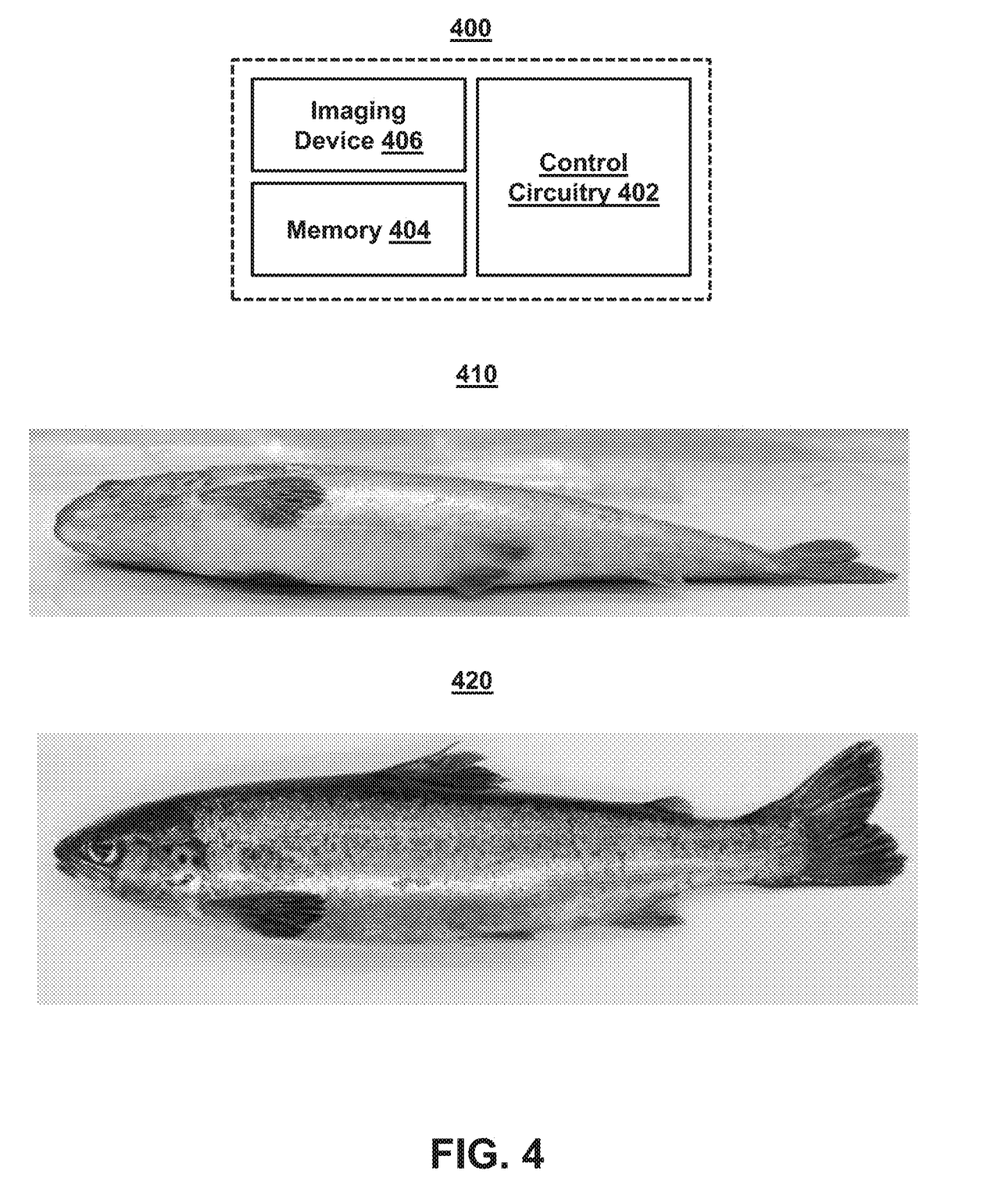
FIG. 4 shows an illustrative example of detecting internal conditions based on external characteristics in fish fries, in accordance with one or more embodiments.

FIG. 4 shows an illustrative example of detecting a genotype biomarker based on phenotype characteristics in fish fries, in accordance with one or more embodiments. FIG. 4 includes computer system 400, which may in some embodiments correspond to system 200 (FIG. 2). For example, computer system 400 may capture an image set (e.g., an image set of a fry including a phenotype characteristic of the fry) using an imaging device 406. Imaging device 406 may be incorporated into and/or accessible by a computer system 400. Computer system 400 also includes memory 404, which may be incorporated into and/or accessible by a computer system 400. In some embodiments, computer system 400 may retrieve the image sets from memory 404.

Computer system 400 also include control circuitry 402. Control circuitry 402 may perform one or more processes (e.g., as described below in relation to FIG. 6) to detect a genotype biomarker based on phenotype characteristics in a fry. Control circuitry 402 may train an artificial neural network (e.g., as described above) in order to detect the genotype biomarker based on one or more data sets (e.g., stored in memory 404). Computer system may receive user inputs (e.g., via client device 204 (FIG. 2)) to determine a genotype biomarker based on phenotype characteristics as indicated by image sets. Computer system may then output the determined genotype (e.g., as output 218 (FIG. 2)).

FIG. 4 also includes view 410 and view 420 of a specimen (e.g., a fry). View 410 and view 420 are each an exemplary image set of a fry weighing 2-4 grams (i.e., under 5 grams). As shown in FIG. 4, the specimen has individual external characteristics and the size, position, color, smoltification, and arrangement of these characteristics, with respect to other external characteristics and the fry as a whole, may indicate the presence of internal conditions. These individual external characteristics are identifiable using view 410 and view 420. For example, as shown in FIG. 4, external characteristics of the fry include the size, location, position, coloration, maturity/development level of the parts of the fry, including the dorsal fin, caudal fin, operculum, pectoral fin, gills, and/or scales. Imaging device 406 may capture one or more image sets. The image sets may be converted into pixel array and used an input for the artificial neural network. In embodiments using the convolutional neural network, the convolution layers may extract features from the input image and preserve the relationship between pixels by learning image features (and their size, location, coloration, maturity/development level) using small squares of input data. For example, the size of the dorsal fin with respect to the caudal fin may indicate an internal condition. In another example, the location of the operculum may indicate another internal condition.

As shown in FIG. 4, the image sets may include one or more angles of the specimen. View 410 is a bottom view and view 420 is a side view. In some embodiments, additional angles may be used based on particular phenotype characteristics of interest. By using multiple angles, computer system 400 may better detect external characteristics of a given specimen. For example, the multiple angles allow for individual phenotype characteristics (e.g., a dorsal fin) to be imaged from different angles, which provides computer system 400 with more complete data. In some embodiments, the image set may also include other features used to identify the specimen (e.g., a serial number, order number, and/or batch number), used to determine the scale of the specimen and/or a part of the specimen (e.g., measurement means for height, length, and/or weight), used to provide a reference point for a given phenotype characteristic (e.g., a color palette used to compare color of the specimen to), and/or used to indicate other information that may be used to classify the specimen (e.g., an indicator of age, maturity level, species, size, etc.).

It should be noted that multiple views of the specimen may be used. The one or more views may create a standardized series of orthographic two-dimensional images that represent the form of the three-dimensional specimen. For example, six views of the specimen may be used, with each projection plane parallel to one of the coordinate axes of the object. The views may be positioned relative to each other according to either a first-angle projection scheme or a third-angle projection scheme. The views may include a side view, front view, top view, bottom, and/or end view. The views may also include plan, elevation, and/or section views.

Figure 5:
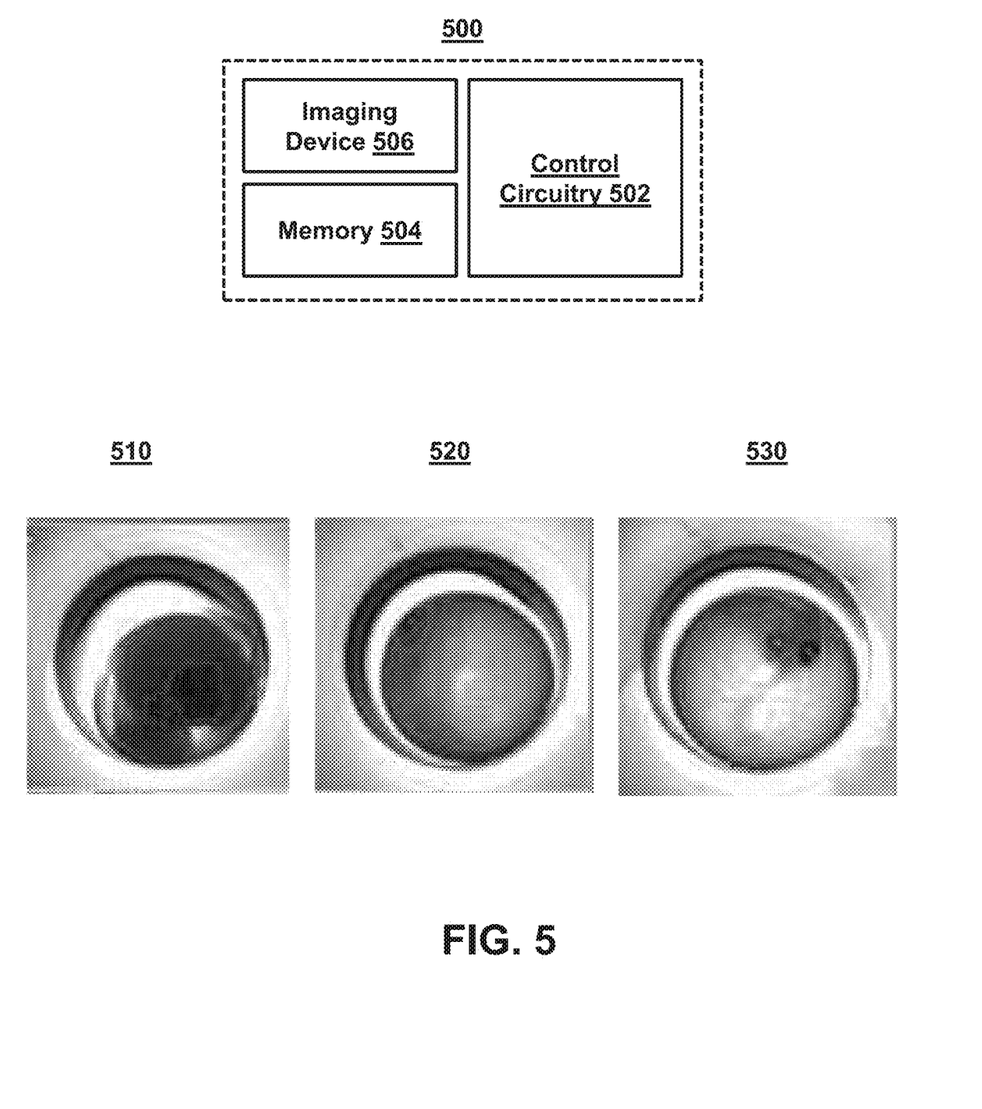
FIG. 5 shows an illustrative example of detecting internal conditions based on external characteristics in fertilized eggs, in accordance with one or more embodiments.

FIG. 5 shows an illustrative example of detecting a genotype biomarker based on phenotype characteristics in fertilized eggs, in accordance with one or more embodiments. FIG. 5 includes computer system 500, which may in some embodiments correspond to system 200 (FIG. 2). For example, computer system 500 may capture an image set (e.g., an image set of fertilized eggs including a phenotype characteristic of the fertilized eggs) using an imaging device 506. Imaging device 506 may be incorporated into and/or accessible by a computer system 500. Computer system 500 also includes memory 504, which may be incorporated into and/or accessible by a computer system 500. In some embodiments, computer system 500 may retrieve the image sets from memory 504.

Computer system 500 also include control circuitry 502. Control circuitry 502 may perform one or more processes (e.g., as described below in relation to FIG. 6) to detect a genotype biomarker based on phenotype characteristics in fertilized eggs. Control circuitry 502 may train an artificial neural network (e.g., as described above) in order to detect the genotype biomarker based on one or more data sets (e.g., stored in memory 504). Computer system may receive user inputs (e.g., via client device 204 (FIG. 2)) to determine a genotype biomarker based on phenotype characteristics as indicated by image sets. Computer system may then output the determined genotype (e.g., as output 218 (FIG. 2)).

FIG. 5 also includes three specimens (e.g., specimen 510, specimen 520, and specimen 530) that may be processed by computer system 500. Specimen 510, specimen 520, and specimen 530 are each an exemplary image set of a fertilized egg, each of which weighs substantially under 10 milligrams. As shown in FIG. 5, each specimen has individual external characteristics and the size, position, and arrangement of these, with respect to other external characteristics and the fertilized egg as a whole, may indicate the presence of internal conditions. For example, in each specimen, the size and placement of the egg parts (e.g., vitelline membrane, chorion, yolk, oil globule, perivitelline space, and/or embryo) with respect to the other egg parts provide indications of the genotype biomarkers.

For example, as shown in FIG. 5, external characteristics of the fertilized egg including the size, location, position, coloration, maturity/development level of the parts of the fertilized egg such as the vitelline membrane, chorion, yolk, oil globule, perivitelline space, and/or embryo. Imaging device 506 may capture one or more image sets. The image sets may be converted into pixel arrays and use an input for an artificial neural network. In embodiments using the convolutional neural network, the convolution layers may extract features from the input image and preserve the relationship between pixels by learning image features (and their size, location, coloration, and/or maturity/development level) using small squares of input data. For example, the size of the vitelline membrane with respect to the chorion may indicate an internal condition. In another example, the location of the oil globule may indicate another internal condition.

In some embodiments, the image set may also include other features used to identify the specimen (e.g., a serial number, order number, and/or batch number), used to determine the scale of the specimen and/or a part of the specimen (e.g., measurement means for height, length, and/or weight), used to provide a reference point for a given phenotype characteristic (e.g., a color palette used to compare color of the specimen to), and/or used to indicate other information that may be used to classify the specimen (e.g., an indicator of age, maturity level, species, size, etc.).

Figure 6:
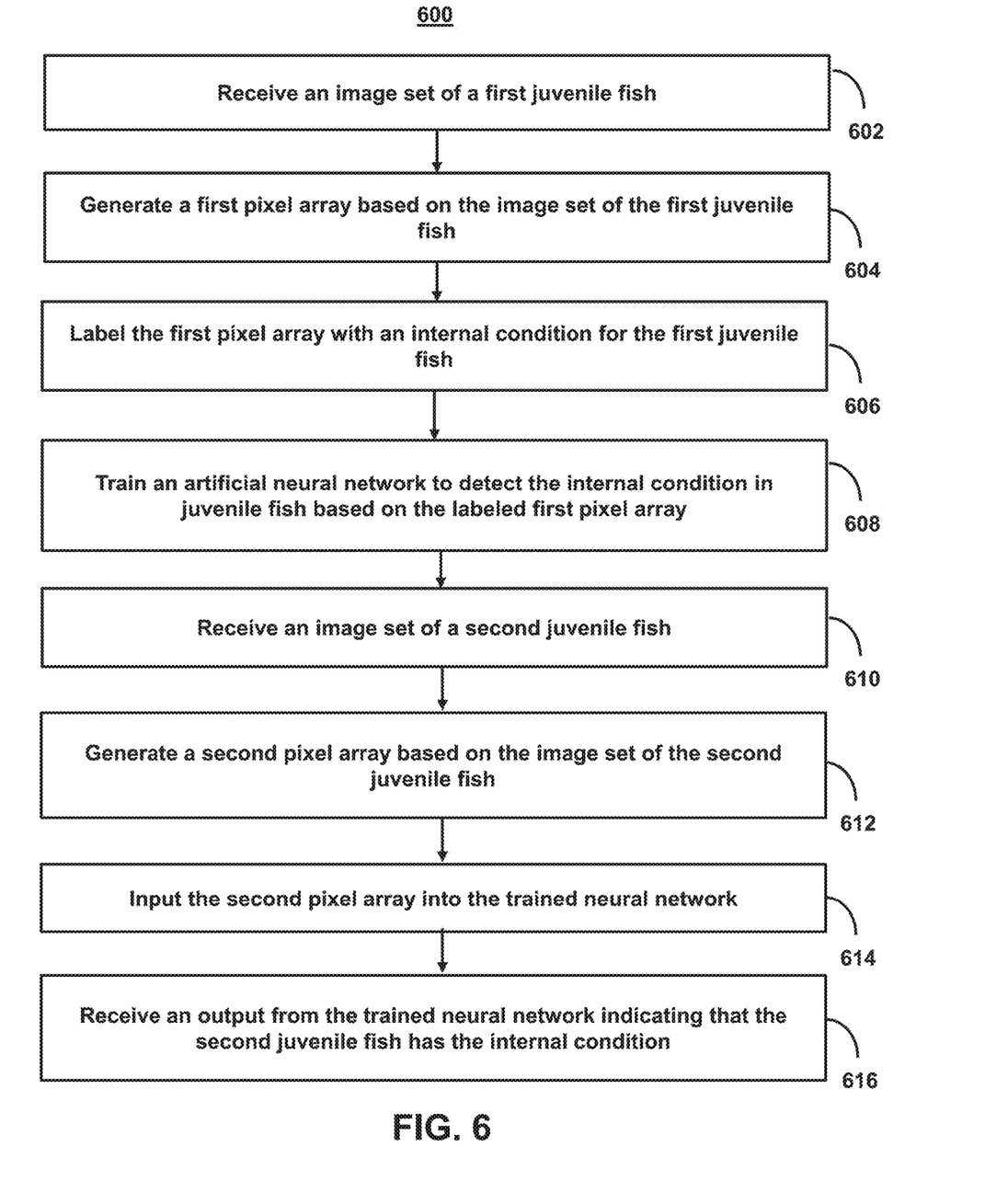
FIG. 6 shows a flowchart for detecting internal conditions based on external characteristics in juvenile fish, in accordance with one or more embodiments.

FIG. 6 shows a flowchart of a process for identifying genotype biomarkers in juvenile fish, in accordance with one or more embodiments. For example, process 600 may represent the steps taken by one or more devices as shown in FIGS. 1-5 for identifying genotype biomarkers in juvenile fish based on phenotype characteristics.

At step 602, process 600 receives (e.g., using control circuitry 402 (FIG. 4) or control circuitry 502 (FIG. 5)) an image set of a first juvenile fish. The image set of the first juvenile fish may include an external characteristic (e.g., a phenotype characteristic) of the first juvenile fish. In some embodiments, the image set may have been captured using an imaging device (e.g., imaging device 406 (FIG. 4) or imaging device 506 (FIG. 5)) incorporated into and/or accessible by a computer system (e.g., computer system 400 (FIG. 4) or computer system 500 (FIG. 5)) for identifying genotype biomarkers in juvenile fish. In some embodiments, the image set may have been retrieved from memory (e.g., memory 404 (FIG. 4) or memory 504 (FIG. 5)) incorporated into and/or accessible by the computer system.

In some embodiments, the juvenile fish may be a fry (as discussed in relation to FIG. 4 above), and the image set of the juvenile fish may include an external first view image of the first fry and an external second view image of the first fry. Additionally or alternatively, the image set of the fry may be generated while the gills of the fry are hydrated or while the fry is sedated in order to reduce stress on the fry. For example, in order to reduce stress on the fry, the image set may be captured while minimizing the time that the fry has been out of the water. This amount of time (e.g., 1 second, 2, seconds, 5-10 seconds, etc.) should be low enough that the gills of the fry do not become dehydrated such that the breathing of the fry is labored. Likewise, in some embodiments, the fry may first enter a liquid sedative solution in which the fry may be sedated prior to the image set being captured. In some embodiments, the juvenile fish may be a fertilized egg (as discussed in relation to FIG. 5 above), and the image set of the juvenile fish may include a depth of field of about half of the fertilized egg.

At step 604, process 600 generates (e.g., using control circuitry 402 (FIG. 4) or control circuitry 505 (FIG. 5)) a first pixel array based on the image set of the first juvenile fish. For example, the detected external characteristic (e.g., phenotype characteristic) in the image set may be converted into a form that can be quickly and efficiently processed by an artificial neural network. In some embodiments, process 600 may include one or more vectors, arrays, and/or matrices that represent either a Red, Green, Blue or grayscale image (e.g., as discussed in relation to FIG. 3). Furthermore, in some embodiments, process 600 may additionally convert the image set from a set of one or more vectors, arrays, and/or matrices to another set of one or more vectors, arrays, and/or matrices. For example, process 600 may convert an image set having a red color array, a green color array, and a blue color to a grayscale color array.

At step 606, process 600 labels (e.g., using control circuitry 402 (FIG. 4) or control circuitry 505 (FIG. 5)) the first pixel array with an internal condition (e.g., a genotype biomarker) for the first juvenile fish. For example, process 600 may include labeling a given specimen with a specimen identifier that can be used to match the genotype biomarker (e.g., as determined from a genetic test of the first juvenile fish) to the first pixel array. In some embodiments, the specimen identifier may indicate a particular x, y coordinates in an image and batch number for the given specimen. For example, in some embodiments, to eliminate bias, process 600 may image multiple specimens together and track to location of a given specimen in an image of multiple specimens. In another example, the specimen identifier may indicate a particular order within a batch.

At step 608, process 600 trains (e.g., using control circuitry 402 (FIG. 4) or control circuitry 502 (FIG. 5)) an artificial neural network to detect the internal condition (e.g., genotype biomarker) in juvenile fish based on the labeled first pixel array. For example, the system may generate the image set of the first juvenile fish, and genetically test the first juvenile fish to determine a genotype biomarker (e.g., SSA0139ECIG, RAD_HT16, rs863507253_ht01, rs863338084, and gender) in the first juvenile fish. Process 600 may then correlate the presence of the genotype biomarker to one or more phenotype characteristics in the image set using the artificial neural network. For example, as discussed in relation to FIG. 3, the artificial neural network may have classifications for the genotype biomarkers. The artificial neural network is then trained based on a first data set (e.g., including data of the first juvenile fish and others) to classify a specimen as having a given genotype biomarker when particular phenotype characteristics are present.

At step 610, process 600 receives (e.g., using control circuitry 402 (FIG. 4) or control circuitry 502 (FIG. 5)) an image set of a second juvenile fish. The image set of the second juvenile fish may include an external characteristic (e.g., a phenotype characteristic) of the second juvenile fish. In some embodiments, the image set of the second juvenile fish may feature the second juvenile fish in the same arrangement and/or position as the first juvenile fish. Additionally or alternatively, other parameters (e.g., axial alignment, image device settings, image quality, etc.) may be the same for the image set of the second juvenile fish as the image set of the fish juvenile fish in order to standardize the image sets. Additionally or alternatively, the step taken to prepare the second juvenile fish prior to the image set being captured (e.g., time out of water, feeding schedule, sedation level) may be the same in order to standardize the image sets. Additionally or alternatively, the batches of juvenile fish for which image sets are to be captured may first be sorted (e.g., based on size, age, maturity level, environmental factors) in order to standardize the image sets. However, in some cases, the juvenile fish may not be sorted or may be actively unsorted to prevent the introduction of bias (e.g., from sorting male and female specimens prior to imaging). For example, process 600 may prevent sorting prior to imaging in order to prevent subtle changes in the imaging parameters to affect the captured images. Process 600 may, in some instances, normalize the image set to account for bias in the system.

At step 612, process 600 generates (e.g., using control circuitry 402 (FIG. 4) or control circuitry 502 (FIG. 5)) a second pixel array based on the image set of the second juvenile fish. For example, as with the first pixel array, the detected external characteristic (e.g., phenotype characteristic) in the image set may be converted into a form that can be quickly and efficiently processed by an artificial neural network. This form may be the same as the form of the first pixel array. In some embodiments, process 600 may normalize the second array in order to account for bias in the system. In some embodiments, this may include one or more vectors, arrays, and/or matrices that represent either a Red, Green, Blue or grayscale image (e.g., as discussed in relation to FIG. 3). Furthermore, in some embodiments, process 600 may additionally convert the image set from a set of one or more vectors, arrays, and/or matrices to another set of one or more vectors, arrays, and/or matrices. For example, process 600 may convert an image set having a red color array, a green color array, and a blue color to a grayscale color array.

At step 614, process 600 inputs (e.g., using control circuitry 402 (FIG. 4) or control circuitry 502 (FIG. 5)) the second pixel array into the trained neural network. For example, as discussed above in relation to FIG. 3, process 600 may input a second data set (e.g., image sets of juvenile fish for which genotype biomarkers are not known) into the trained artificial neural network. The trained artificial neural network may then classify the image sets of juvenile fish into according to the genotype biomarkers. For example, the genotype biomarker for the first juvenile fish may be a first classification of the neural network, and the system may generate an output from the neural network indicating the second juvenile fish has the same genotype biomarker as the first juvenile fish based on matching the second pixel array to the first classification.

At step 616, process 600 outputs (e.g., using control circuitry 402 (FIG. 4) or control circuitry 502 (FIG. 5)) from the trained neural network indicating that the second juvenile fish has the internal condition (e.g., the genotype biomarker). For example, process 600 may determine that based on the second pixel array, the second juvenile fish is included in the same classification as the first juvenile fish. Because the first juvenile fish is determined to have a given genotype biomarker, process 600 determines that the second juvenile fish has the same genotype biomarker.

In some embodiments, process 600 may further handle, sort, and/or transfer the juvenile fish (e.g., for vaccination, gender segregation, transfer to sea or breeding area, etc.) automatically. In such embodiments, the internal condition may be detected based on external characteristics in real-time (e.g., as the juvenile fish are transported along a conveyor belt or otherwise transferred). That is, following the output of an internal condition (e.g., a genotype biomarker as described in FIG. 6 below), process 600 may sort the juvenile fish based on the determined internal condition. For example, a juvenile fish determined to have a first internal characteristic may be sorted into a first group, and a juvenile fish determined to have a second internal characteristic may be sorted into a second group.

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 1-5 could be used to perform one or more of the steps in FIG. 6.

Although the present invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The present techniques will be better understood with reference to the following enumerated embodiments:

1. A method of identifying internal conditions in juvenile fish based on external characteristics, the method comprising: receiving, using control circuitry, an image set of a first juvenile fish, wherein the image set of the first juvenile fish includes a phenotype characteristic of the first juvenile fish; generating, using the control circuitry, a first pixel array based on the image set of the first juvenile fish; labeling, using the control circuitry, the first pixel array with a genotype biomarker for the first juvenile fish; training, using the control circuitry, an artificial neural network to detect the genotype biomarker in juvenile fish based on the labeled first pixel array; receiving, using the control circuitry, an image set of a second juvenile fish, wherein the image set of the second juvenile fish includes a phenotype characteristic of the second juvenile fish; generating, using the control circuitry, a second pixel array based on the image set of the second juvenile fish; inputting, using the control circuitry, the second pixel array into the trained neural network; and receiving, using the control circuitry, an output from the trained neural network indicating that the second juvenile fish has the genotype biomarker.

2. The method of embodiment 1, wherein the first juvenile fish is a first fry and the second juvenile fish is a second fry, and wherein the image set of the first juvenile fish includes an external first view image of the first fry and an external second view image of the first fry and the image set of the second juvenile fish includes an external first view image of the second fry and an external second view image of the second fry.

3. The method of embodiment 2, wherein the image set of the first juvenile fish is generated while the gills of the first juvenile fish are hydrated or while the first juvenile fish is sedated.

4. The method of claim 1, wherein the first juvenile fish is a first fertilized fish egg and the second juvenile fish is a second fertilized fish egg, and wherein the image set of the first juvenile fish includes an image of the first fertilized egg with a depth of field of about half of the first fertilized egg and the image set of the second juvenile fish includes an image of the first fertilized egg with a depth of field of about half of the second fertilized egg.

5. The method of any of embodiments 1-4, further comprising: receiving an image set of a third juvenile fish, wherein the image set of the third juvenile fish includes a phenotype characteristic of the third juvenile fish; generating a third pixel array based on the image set of the third juvenile fish; labeling the third pixel array with a genotype biomarker for the third juvenile fish; training the neural network to detect genotype biomarkers in juvenile fish based on the labeled first pixel array and the labeled second pixel array.

6. The method of any of embodiments 1-5, wherein the genotype biomarker for the first juvenile fish is a first classification of the neural network, and wherein receiving the output from the neural network indicating the genotype biomarker for the second juvenile fish comprises matching the second pixel array to the first classification.

7. The method of any of embodiments 1-6, wherein the image set of the first juvenile fish and the image set of the second juvenile fish were generated together, and wherein the first juvenile fish is male and the second juvenile fish is female.

8. The method of any of embodiments 1-7, wherein the image set of the first juvenile fish is created using an imaging device that detects electromagnetic radiation with wavelengths between about 400 nanometers to about 1100 nanometers.

9. The method of any of embodiments 1-8, wherein the image set of the first juvenile fish has a red color array, a green color array, and a blue color array, and wherein generating the first pixel array based on the image set of the first juvenile fish, further comprises: determining a grayscale color array for the image set of the first juvenile fish; and generating the first pixel array based on the grayscale color array.

10. The method of any of embodiments 1-9, further comprising: generating the image set of the first juvenile fish; and genetically testing the first juvenile fish to determine the genotype biomarker in the first juvenile fish.

11. The method of any of embodiments 1-10, wherein the first juvenile fish is under 50 grams, and wherein the second juvenile fish is under 5 grams.

12. A tangible, non-transitory, machine-readable medium storing instructions that, when executed by a data processing apparatus, cause the data processing apparatus to perform operations comprising those of any of embodiments 1-10.

13. A system comprising: one or more processors; and memory storing instructions that, when executed by the processors, cause the processors to effectuate operations comprising those of any of embodiments 1-10.

What is claimed is:
1. A method comprising:
receiving, using control circuitry, an image set of a first juvenile salmonid, wherein the image set of the first juvenile salmonid includes a phenotype characteristic of the first juvenile salmonid;
generating, using the control circuitry, a first pixel array based on the image set of the first juvenile salmonid;
labeling, using the control circuitry, the first pixel array with a genotype biomarker for the first juvenile salmonid, the genotype biomarker associated with gender and/or resistance to Infection Pancreatic Necrosis;
training, using the control circuitry, an artificial neural network to detect the genotype biomarker in juvenile salmonids based on the labeled first pixel array;
receiving, using the control circuitry, an image set of a second juvenile salmonid, wherein the image set of the second juvenile salmonid includes a phenotype characteristic of the second juvenile salmonid;
generating, using the control circuitry, a second pixel array based on the image set of the second juvenile salmonid;
inputting, using the control circuitry, the second pixel array into the trained neural network; and
receiving, using the control circuitry, an output from the trained neural network indicating that the second juvenile salmonid has the genotype biomarker associated with gender and/or resistance to Infection Pancreatic Necrosis.

2. The method of claim 1, wherein the first juvenile salmonid is a first fry and the second juvenile salmonid is a second fry, and wherein the image set of the first juvenile salmonid includes an external first view image of the first fry and an external second view image of the first fry and the image set of the second juvenile salmonid includes an external first view image of the second fry and an external second view image of the second fry.

3. The method of claim 2, wherein the image set of the first juvenile salmonid is generated while gills of the first juvenile salmonid are hydrated or while the first juvenile salmonid is sedated.

4. The method of claim 1, further comprising:
receiving an image set of a third juvenile salmonid, wherein the image set of the third juvenile salmonid includes a phenotype characteristic of the third juvenile salmonid;
generating a third pixel array based on the image set of the third juvenile salmonid;

labeling the third pixel array with a genotype biomarker for the third juvenile salmonid; and training the neural network to detect genotype biomarkers in juvenile salmonids fish based on the labeled first pixel array and the labeled third pixel array.

5. The method of claim 4, wherein the genotype biomarker for the first juvenile salmonid is a first classification of the neural network, and wherein receiving the output from the neural network indicating the genotype biomarker for the second juvenile salmonid comprises matching the second pixel array to the first classification.

6. The method of claim 4, wherein the image set of the first juvenile salmonid and the image set of the second juvenile salmonid were generated together, and wherein the first juvenile salmonid is male and the second juvenile salmonid is female.

7. The method of claim 1, wherein the image set of the first juvenile salmonid is created using an imaging device that detects electromagnetic radiation with wavelengths between 400 nanometers to 1100 nanometers.

8. The method of claim 1, wherein the image set of the first juvenile salmonid has a red color array, a green color array, and a blue color array, and wherein generating the first pixel array based on the image set of the first juvenile salmonid, further comprises:
determining a grayscale color array for the image set of the first juvenile salmonid; and
generating the first pixel array based on the grayscale color array.

9. The method of claim 1, further comprising:
generating the image set of the first juvenile salmonid; and
genetically testing the first juvenile salmonid to determine the genotype biomarker in the first juvenile salmonid.

10. The method of claim 1, wherein the image set of the first juvenile salmonid includes first ultrasound images and the image set of the second juvenile salmonid includes second ultrasound images.

11. The method of claim 1, wherein the image set of the first juvenile salmonid includes first red green blue (RGB) images and the image set of the second juvenile salmonid includes second RGB images.

12. The method of claim 1, wherein the image set of the first juvenile salmonid includes first grayscale images and the image set of the second juvenile salmonid includes second grayscale images.

13. The method of claim 1, wherein the genotype biomarker is further associated with, resistance to infection and disease, early sexual maturation, and/or growth rate.

14. The method of claim 1, further comprising automatically sorting the second juvenile salmonid, in real-time based on the output from the trained neural network, into a first group of juvenile salmonids determined to have the genotype biomarker, or a second group of juvenile salmonids that do not have the genotype biomarker.

15. A system comprising:
memory configured to store an artificial neural network; and
control circuitry configured to:
receive an image set of a first juvenile salmonid, wherein the image set of the first juvenile salmonid includes a phenotype characteristic of the first juvenile salmonid;
generate a first pixel array based on the image set of the first juvenile salmonid;
label the first pixel array with a genotype biomarker for the first juvenile salmonid, the genotype biomarker associated with gender and/or resistance to Infection Pancreatic Necrosis;
train an artificial neural network to detect the genotype biomarker in juvenile salmonids based on the labeled first pixel array;
receive an image set of a second juvenile salmonid, wherein the image set of the second juvenile salmonid includes a phenotype characteristic of the second juvenile salmonid;
generate a second pixel array based on the image set of the second juvenile salmonid;
input the second pixel array into the trained neural network;
receive an output from the trained neural network indicating that the second juvenile salmonid has the genotype biomarker associated with gender and/or resistance to Infection Pancreatic Necrosis.

16. The system of claim 15, wherein the first juvenile salmonid is a first fry and the second juvenile salmonid is a second fry, and wherein the image set of the first juvenile salmonid includes an external first view image of the first fry and an external second view image of the first fry and the image set of the second juvenile salmonid includes an external first view image of the second fry and an external second view image of the second fry.

17. The system of claim 16, wherein the image set of the first juvenile salmonid is generated while gills of the first juvenile salmonid are hydrated or while the first juvenile salmonid is sedated.

18. The system of claim 15, wherein the control circuitry is further configured to:
receive an image set of a third juvenile salmonid, wherein the image set of the third juvenile salmonid includes a phenotype characteristic of the third juvenile salmonid;
generate a third pixel array based on the image set of the third juvenile salmonid;
label the third pixel array with a genotype biomarker for the third juvenile salmonid; and
train the neural network to detect genotype biomarkers in juvenile salmonids fish based on the labeled first pixel array and the labeled third pixel array.

19. The system of claim 18, wherein the genotype biomarker for the first juvenile salmonid is a first classification of the neural network, and wherein receiving the output from the neural network indicating the genotype biomarker for the second juvenile salmonid comprises matching the second pixel array to the first classification.

20. The system of claim 18, wherein the image set of the first juvenile salmonid and the image set of the second juvenile salmonid were generated together, and wherein the first juvenile salmonid is male and the second juvenile salmonid is female.

21. The system of claim 15, wherein the image set of the first juvenile salmonid is created using an imaging device that detects electromagnetic radiation with wavelengths between 400 nanometers to 1100 nanometers.

22. The system of claim 15, wherein the image set of the first juvenile salmonid has a red color array, a green color array, and a blue color array, and wherein generating the first pixel array based on the image set of the first juvenile salmonid, wherein the control circuitry is further configured to:
determine a grayscale color array for the image set of the first juvenile salmonid; and generate the first pixel array based on the grayscale color array.

23. The system of claim 15, wherein the control circuitry is further configured to:
generate the image set of the first juvenile salmonid; and
genetically test the first juvenile salmonid to determine the genotype biomarker in the first juvenile salmonid.

24. The system of claim 15, wherein the image set of the first juvenile salmonid includes first ultrasound images and the image set of the second juvenile salmonid includes second ultrasound images.

25. The system of claim 15, wherein the image set of the first juvenile salmonid includes first red green blue (RGB) images and the image set of the second juvenile salmonid includes second RGB images.

26. The system of claim 15, wherein the image set of the first juvenile salmonid includes first grayscale images and the image set of the second juvenile salmonid includes second grayscale images.

27. The system of claim 15, wherein the genotype biomarker is further associated with, resistance to infection and disease, early sexual maturation, and/or growth rate.

28. The system of claim 15, wherein the control circuitry is further configured to automatically sort the second juvenile salmonid, in real-time based on the output from the trained neural network, into a first group of juvenile salmonids determined to have the genotype biomarker, or a second group of juvenile salmonids that do not have the genotype biomarker.

\* \* \* \* \*